United States Patent
Leak et al.

(10) Patent No.: US 9,333,303 B2
(45) Date of Patent: May 10, 2016

(54) DRUG DELIVERY DEVICE HAVING A TRIGGER

(75) Inventors: David Martin Leak, Lake Hopatcong, NJ (US); Malcolm Stanley Boyd, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 338 days.

(21) Appl. No.: 13/885,327
(22) PCT Filed: Nov. 28, 2011
(86) PCT No.: PCT/EP2011/071108
§ 371 (c)(1), (2), (4) Date: May 14, 2013
(87) PCT Pub. No.: WO2012/072533
PCT Pub. Date: Jun. 7, 2012

(65) Prior Publication Data
US 2013/0231613 A1    Sep. 5, 2013

Related U.S. Application Data

(60) Provisional application No. 61/432,713, filed on Jan. 14, 2011.

(30) Foreign Application Priority Data

Nov. 29, 2010   (EP) .................................... 10192840

(51) Int. Cl.
*A61M 5/315* (2006.01)
*A61M 5/19* (2006.01)
*A61M 5/20* (2006.01)

(52) U.S. Cl.
CPC ............ *A61M 5/31596* (2013.01); *A61M 5/19* (2013.01); *A61M 5/20* (2013.01); *A61M 5/31551* (2013.01); *A61M 5/31575* (2013.01); *A61M 5/31583* (2013.01); *A61M 5/31585* (2013.01); *A61M 5/2066* (2013.01)

(58) Field of Classification Search
CPC ..... A61M 5/19; A61M 5/20; A61M 5/31596; A61M 5/31575; A61M 5/31583
See application file for complete search history.

(56) References Cited

U.S. PATENT DOCUMENTS

| 4,755,169 | A | | 7/1988 | Sarnoff et al. |
| 5,584,815 | A | * | 12/1996 | Pawelka et al. ............... 604/191 |
| 6,917,828 | B2 | | 7/2005 | Fukuda |
| 2010/0143864 | A1 | | 6/2010 | An |

FOREIGN PATENT DOCUMENTS

WO    2004/108193    12/2004

OTHER PUBLICATIONS

Chinese Office Action for CN Application No. 201180066274.5, dated Aug. 29, 2014.
International Preliminary Report on Patentability for Int. App. No. PCT/EP2011/071108, mailed Jun. 13, 2013.
International Search Report and Written Opinion for Int. App. No. PCT/EP2011/071108, completed Jan. 4, 2012.

* cited by examiner

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A drug delivery device having a trigger biasing member that provides dispense assistance. The drug delivery device includes a variable dose setting mechanism that is operably coupled to a primary reservoir holding a first medicament. The drug delivery device also includes a fixed dose setting mechanism that is operably coupled to a secondary reservoir holding a second medicament. The fixed dose setting mechanism comprises a trigger biasing member or spring. In addition, the drug delivery device includes a mechanical coupling that operably couples the variable dose setting mechanism and the fixed dose setting mechanism. During dose setting, activation of a single dose setter sets a variable dose of the first medicament. Setting of a minimum dose of the first medicament causes a fixed dose of the second medicament to be automatically set, and, during dispense, the trigger spring at least assists with the dispense of the fixed dose of the second medicament.

14 Claims, 5 Drawing Sheets

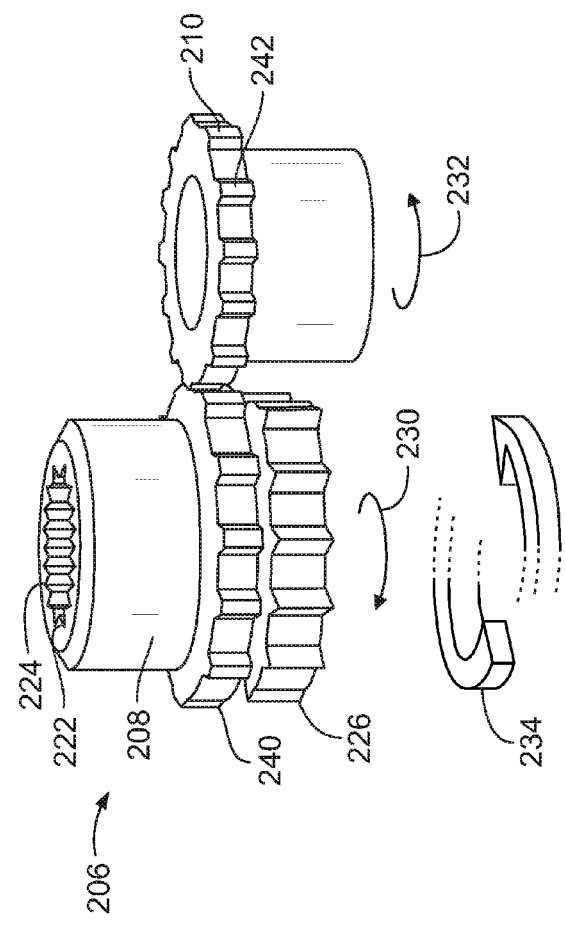
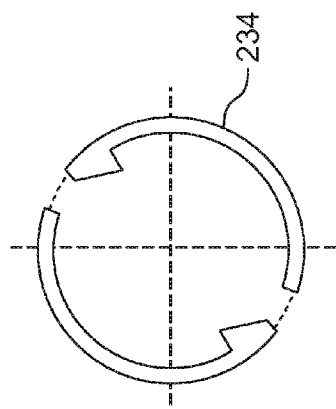
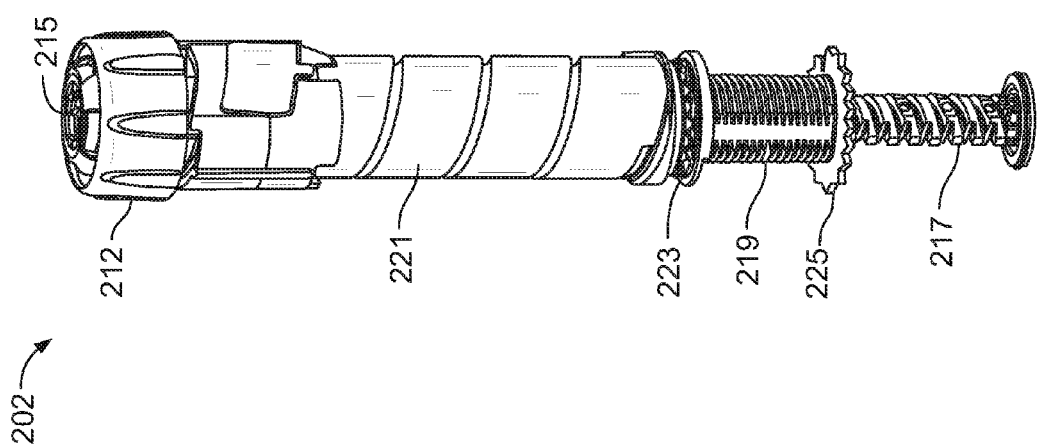
FIG. 5A
FIG. 5B
FIG. 4

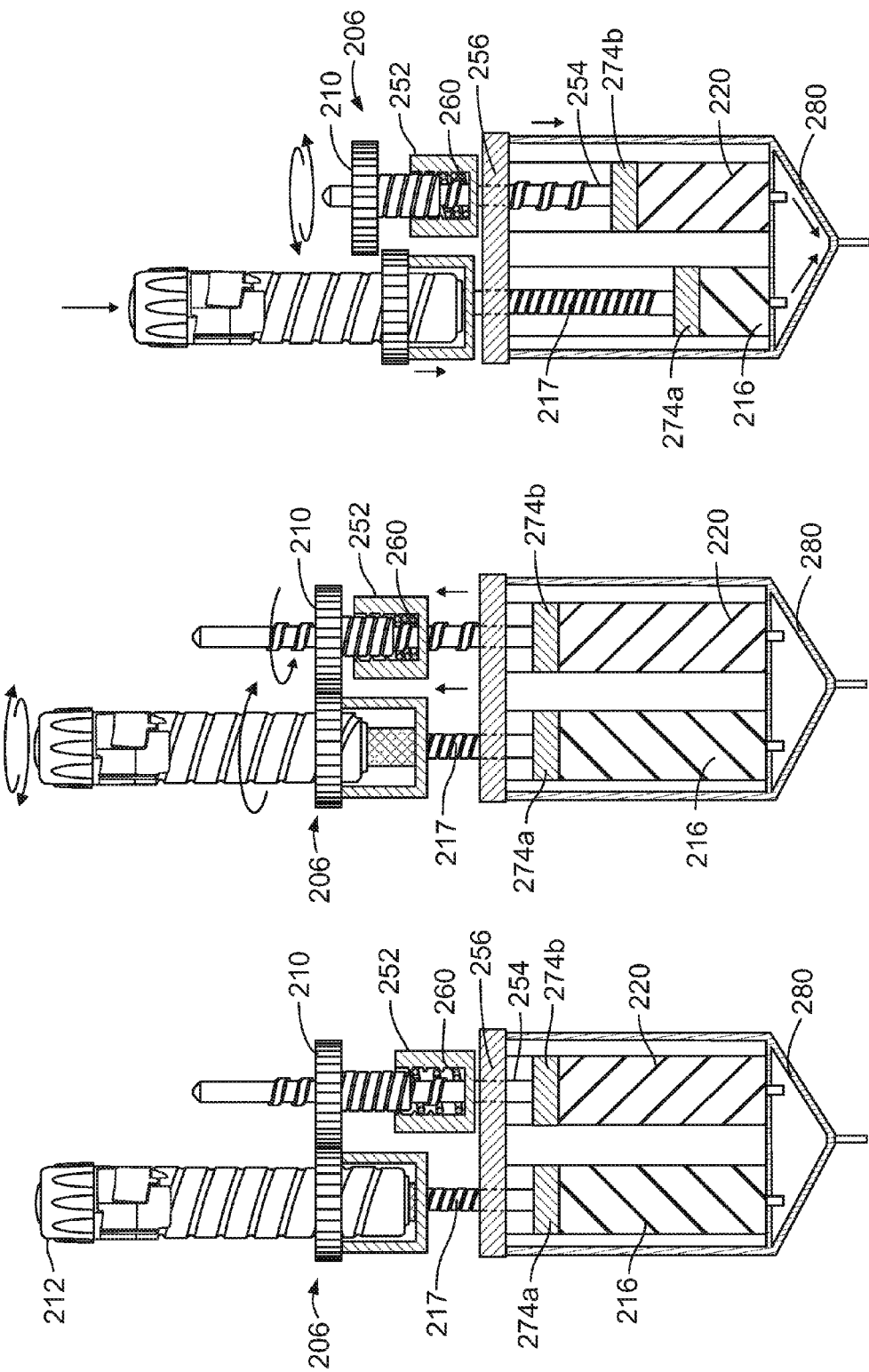

DRUG DELIVERY DEVICE HAVING A TRIGGER

CROSS REFERENCE TO RELATED APPLICATIONS

The present application is a U.S. National Phase Application pursuant to 35 U.S.C. §371 of International Application No. PCT/EP2011/071108 filed Nov. 28, 2011, which claims priority to European Patent Application No. 10192840.6 filed Nov. 29, 2010 and U.S. Provisional Patent Application No. 61/432,713, filed Jan. 14, 2011. The entire disclosure contents of these applications are herewith incorporated by reference into the present application.

FIELD OF THE DISCLOSURE

This present patent application relates to medical devices and methods of delivering at least two drug agents from separate reservoirs using devices having only a single dose setting mechanism and a single dispense interface. A single delivery procedure initiated by the user causes a non-user settable dose of a second drug agent and a user-variable set dose of a first drug agent to be delivered to the patient. The drug delivery device may include a trigger biasing member, preferably a spring, that is configured to assist with the delivery of the second drug agent. The drug agents are contained in two or more multiple dose reservoirs, containers or packages, each containing independent (single drug compound) or pre-mixed (co-formulated multiple drug compounds) drug agents. The disclosed method and system is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. The disclosed method and system is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties.

An additional issue that may arise is a potentially high dispense force required to inject a drug compound or two drug compounds. Dispense force is generally proportional to the amount of fluid being dispensed over a given time and the resistance (e.g., hydraulic resistance) through the device. A higher dose may therefore require a higher dispense force. Further, because a dual injection device injects two drug compounds rather than a single drug compound, the dispense force required by a dual injection device may be higher than a dispense force required by a typical single compound drug delivery device. For instance, dual injection devices may also have to overcome two sets of delivery mechanism frictions or two bungs moving in two cartridges.

Fully automatic devices may reduce or eliminate the force required to inject a drug compound or two drug compounds. However, fully automatic devices that have the capability to fully inject all drug compounds may experience 'push-back' from some users due to the lack of user control during dispensing. For example, certain users/patients express the desire or need to have at least a given level of control over the dispensing process (e.g., be required to use some manual input to dispense the drugs). Fully automatic devices have the further disadvantage of having to exert a high magnitude of force to account for the force variability and the requirement to ensure sufficient margin between the force delivered and the force required in all dose scenarios.

Accordingly, there exists a strong need to provide devices and methods for the delivery of two or more medicaments in a single injection or delivery step that is simple for the user to perform. Further, there exists a need to provide devices and methods that reduce the dispense force for delivery of two or more medicaments in a single injection or delivery step, while at the same time allowing the user a degree of control over the dispense.

The disclosed method and system overcomes the above-mentioned problems by providing separate storage containers for two or more active drug agents that are then only combined and/or delivered to the patient during a single delivery procedure. The disclosed method and system also provides a trigger, that is operably connected to a biasing member, such as a spring, that is configured to reduce the dispense force required by the device. Setting a dose of one medicament automatically fixes or determines the dose of the second medicament (i.e. non-user settable). The disclosed method and system also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. Alternatively, the second fluid quantity can be changed by varying the properties of the fixed dose mechanism. The disclosed system and method may achieve a wide variety of target therapeutic profiles. For example, the disclosed system and method may achieve a therapeutic profile that delivers a fixed dose of a secondary medicament once a minimum setting threshold dose of a primary medicament has been set. The disclosed system and method also may add an element of auto-assistance that reduces the dispense force for the injection of two (or more) drug compounds while allowing the user a degree of control over the dispense process.

These and other advantages will become evident from the following more detailed description of the invention.

SUMMARY

The disclosed system and method allows complex combination of multiple drug compounds (i.e., medicaments) within a single device. The disclosed system and method may achieve a therapeutic profile that delivers a fixed dose of a secondary medicament once a minimum threshold dose of a primary medicament has been set. The disclosed system and method also provides for auto-assistance that reduces the dispense force for the injection of multiple drug compounds within the single device. In particular, the disclosed system and method allows the user to set and dispense a multi-drug compound device through one single dose setting mechanism and a single dispense interface, and the system includes a trigger spring that provides auto-assistance that reduces the overall combined dispense force. This single dose setter controls the dose setting mechanisms of the device such that a predefined combination of the individual drug compounds is delivered when a single minimum dose of one of the medicaments is set and dispensed through the single dispense interface. Although principally described in this application as an injection device, the basic principle could be applicable to other forms of drug delivery, such as, but not limited to, inhalation, nasal, ophthalmic, oral, topical, and like devices.

By defining the therapeutic relationship between the individual drug compounds, Applicants' delivery device would help ensure that a patient/user receives the optimum therapeutic combination dose from a multi-drug compound device without the inherent risks associated with multiple inputs, where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

This disclosed system is of particular benefit to users with dexterity or computational difficulties as the single input and associated predefined therapeutic profile removes the need for them to calculate their prescribed dose every time they use the device and the single input allows considerably easier setting and dispensing of the combined compounds.

In an embodiment of the proposed system, a master drug compound, such as insulin, is contained within a primary reservoir and a secondary medicament is contained within a secondary reservoir. When a dose of the primary compound is set and dispensed, the secondary compound is set and delivered. Although Applicants' present patent application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed system and method.

For the purposes of Applicants' system and method the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(ω-carboxyheptadecanoyl) human insulin.

As used herein the term "GPL-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys- Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of Applicants' disclosure relates to a drug delivery system to deliver two or more medicaments through a single dose setter and a single dispense interface, where the device has a housing containing a single user-operable dose setter operably connected to a primary reservoir of a first medicament containing multiple doses of at least one drug agent. A dose button is operably connected to the primary reservoir of medicament and a single dispense interface is configured for fluid communication with the primary reservoir. A secondary reservoir of a second medicament containing multiple doses of at least one drug agent is configured for fluid communication to the single dispense interface. A single activation of the dose setter by a user sets a dose from the primary reservoir and automatically sets a non-user settable dose of the second medicament. A single activation of the dose button causes the set dose of the first medicament from the primary reservoir and the set non-user settable dose of the second medicament to be expelled through the single dispense interface. The secondary reservoir may be operably connected to a trigger spring that is configured to assist with dispense of the secondary medicament.

This dose button can be any type of mechanism that triggers the delivery procedure. Applicants' system has a single dispense interface configured for fluid communication with the primary reservoir and with a secondary reservoir of medicament containing at least one drug agent. The drug dispense interface can be any type of outlet that allows the two or more medicaments to exit the system and be delivered to the patient. Types of interfaces include hollow needles, catheters, atomizers, pneumatic injectors, or needle-less injectors, mouthpieces, nasal-applicators and the like interfaces.

The secondary reservoir contains multiple doses of medicament. The system is designed such that a single activation of the dose button causes the user set dose of medicament from the primary reservoir and a non-user set dose of medicament from the second reservoir to be expelled through the single dispense interface. By user settable dose it is meant dose that the user (patient or health care provider) can physically manipulate the device to set a desired dose. Additionally, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. In other words, when the user (or another input as described above) sets the dose of the primary medicament in the primary reservoir, the dose of the second medicament is automatically set.

In an example of Applicants' proposed system, a drug delivery device includes a variable dose setting mechanism that is operably coupled to a primary reservoir holding a first medicament. The drug delivery device also includes a fixed dose setting mechanism that is operably coupled to a secondary reservoir holding a second medicament. The fixed dose setting mechanism comprises a trigger spring. The drug delivery device further includes a single dose setter operably coupled to the variable dose setting mechanism. In addition, the drug delivery device includes a mechanical coupling that operably couples the variable dose setting mechanism and the fixed dose setting mechanism. During dose setting, activation of the single dose setter sets a variable dose of the first medicament. Setting of a minimum dose of the first medicament causes a fixed dose of the second medicament to be automatically set, and, during dispense, the trigger spring at least assists with the dispense of the fixed dose of the second medicament.

In an example, the mechanical coupling comprises (i) a drive gear and (ii) a driven gear. The drug delivery device further comprises a drive collar that is capable of engagement with the driven gear. In this example, the trigger spring is operably coupled to the drive collar. Further, automatically setting the fixed dose comprises the drive gear driving the driven gear, wherein driving the driven gear causes the driven gear to lift the drive collar, and wherein lifting of the drive collar compresses the trigger spring. During dispense, the drive gear and the driven gear disengage from one another, and the compressed trigger spring forces the drive collar downward to assist with the dispense of the second medicament.

Applicants' present disclosure also covers a method of dispensing a fixed dose of one medicament and a variable dose of a second medicament from separate reservoirs that involves the steps of first setting a dose of a first medicament contained in a primary reservoir of a drug delivery device having a single dose setter. This setting of the first dose automatically sets the dose from a secondary reservoir (e.g., after a minimum first dose threshold is exceeded) without a separate input by the user. Next a dose button is activated that moves both the set dose of the first medicament from the primary reservoir and the automatically set non-user settable dose from the secondary reservoir through a single dispense interface. The method further comprises compressing a trigger spring element during setting of the user settable dose.

The combination of compounds as discrete units or as a mixed unit can be delivered to the body via an integral needle. This would provide a combination drug injection system that, from a user's perspective, would be achieved in a manner that very closely matches the currently available injection devices that use standard needles. One possible delivery procedure would involve the following steps:

Attach a single dispense interface, such as a needle hub, to the distal end of the injection device such that the proximal end of the single dispense interface is in fluidic communication with both the primary compound and secondary compound.

Dial up (i.e., set) the injection device such that it is ready to dispense the desired dose of the primary compound. As the single dose setter sets the dose of the primary compound, a predefined non-user settable dose of the secondary compound is automatically set at the same time. Further, a trigger spring is compressed during this action.

Insert or apply the distal end of the single dispense interface to the patient at or into the desired administration site. Dose the primary compound by activating a single dose button, which also causes the secondary compound to automatically dispense, with auto-assistance provided by the compressed trigger spring to reduce the dispense force.

The drug delivery system of Applicants' disclosure may be designed in such a way as to limit its use to exclusive primary and secondary reservoirs through employment of dedicated or coded features.

A particular benefit of Applicants' proposed system and method is that the use of two multi-dose reservoirs makes it is possible to tailor dose regimes when required, especially where a titration period is necessary for a particular drug. In an example, a set of drug delivery devices may be provided that have second dose setting mechanisms and/or reservoirs that have different properties, and thus result in different fixed doses of a second medicament. The drug delivery devices could be supplied in a number of titration levels with obvious differentiation features such as, but not limited to, aesthetic design of features or graphics, numbering etc, so that a user could be instructed to use the supplied drug delivery devices in a specific order to facilitate titration. Alternatively, the prescribing physician may provide the patient with a number of "level one" titration drug delivery devices and then when these were finished, the physician could then prescribe the next level.

Another particular benefit of Applicants' proposed system is that the system provides an element of auto-assistance that reduces the dispense force for the injection of two (or more) drug compounds while allowing the user a degree of control over the dispense process.

A further feature of an example of Applicants' proposed system and method is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 4 illustrates example components of a variable dose setting mechanism of the drug delivery device illustrated in FIG. 3;

FIG. 5a is a perspective view of the mechanical coupling of the drug delivery device illustrated in FIG. 3;

FIG. 5b is a cross-sectional view of ratchet features on the device body of the drug delivery device illustrated in FIG. 3;

FIGS. 9a-c depict the drug delivery device illustrated in FIG. 3 in various operational phases.

DETAILED DESCRIPTION

Figure 1:
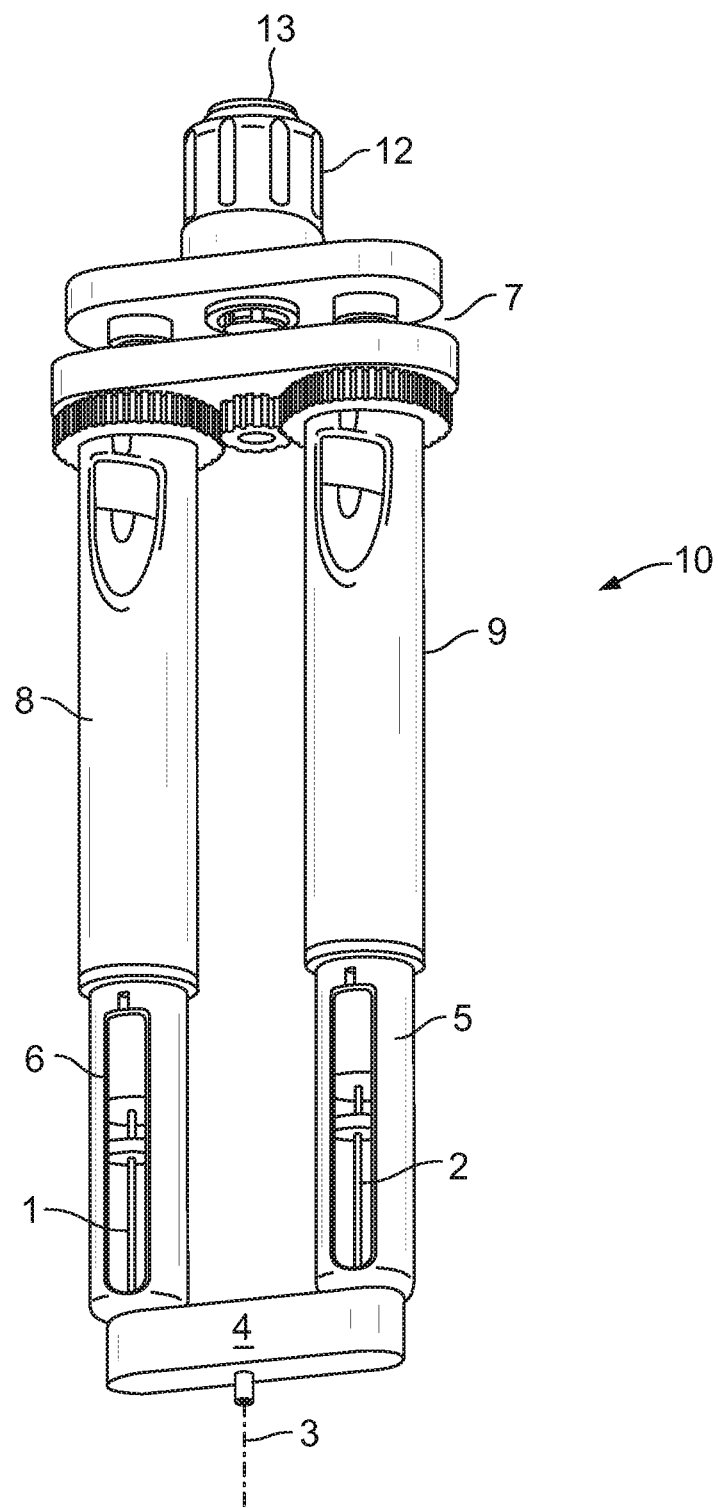
FIG. 1 illustrates an example drug delivery system, the drug delivery system having two multi-dose reservoirs positioned side-by-side containing a primary medicament and a secondary medicament, respectively.
Figure 3:
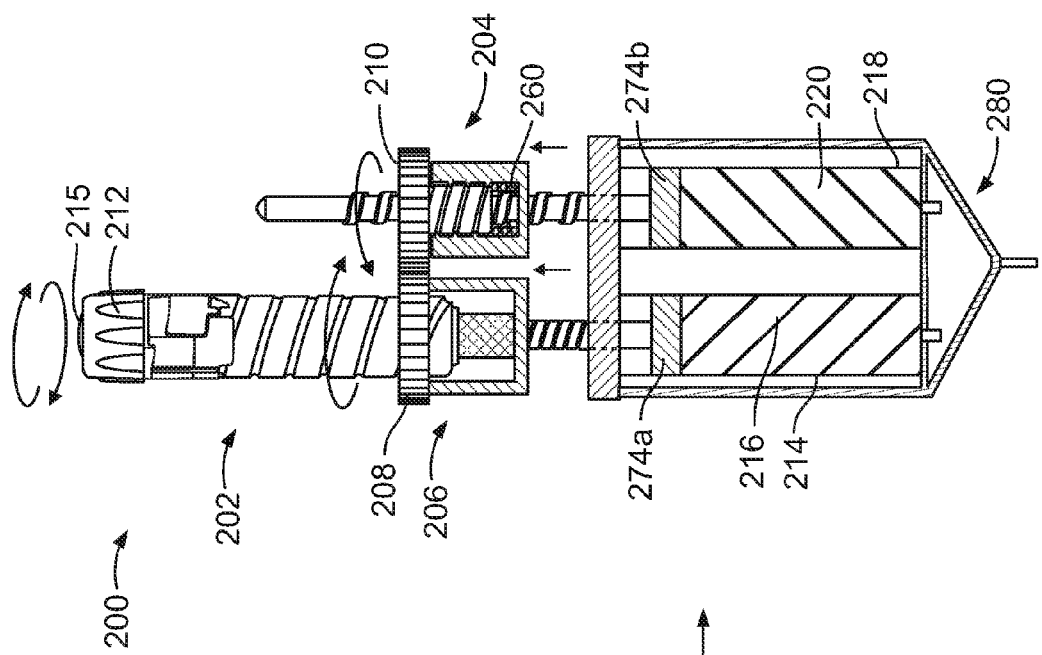
FIG. 3 illustrates an example drug delivery device in accordance with an embodiment of Applicants' proposed concept.

The drug delivery system of the present disclosure administers a non-user settable (i.e., fixed or predetermined) dose of a second medicament (i.e., secondary drug compound) and a variable dose of a first medicament (i.e., primary drug compound) through a single output or drug dispense interface. Setting the dose of the primary medicament by the user automatically determines the fixed dose of the second medicament. In an example the drug dispense interface is a needle cannula (hollow needle). FIG. 1 generally illustrates a multi-dose injection device that is capable of setting and delivering both a dose of a first medicament and a dose of a second medicament via a single dose setter and a single dispense interface. Such an injection device may be modified to include a biasing element (e.g., a trigger spring) that is capable of assisting with delivery of the medicament. FIG. 3 illustrates an example drug delivery device according to Applicant's proposed concept that includes a trigger spring and is capable of assisting with delivery of the medicament.

In particular, FIG. 1 illustrates one possible example of a drug delivery system, where a multi-use injection device 10 has two reservoirs that are positioned side-by-side with one containing a first medicament 1 and the other a second medicament 2. These reservoirs may contain multiple doses of each medicament. Each reservoir may be self-contained and provided as sealed and sterile cartridges. These cartridges can be of different volumes and replaceable when empty or they can be fixed (non-removable) in the system. They can also have pierceable seals or septa to accept needle cannula.

The cartridges may be housed in cartridge holders 5 and 6 that have attachment means compatible with a removable, disposable hub or housing 4 that contains the single dispense interface. In this example the single dispense interface is shown as output needle 3. The hub can be of any design, provided that it allows for fluid communication between the primary and secondary medicaments and the single dispense interface or needle 3. An example design of hub 4 would include what is referred to in the art as a "2-to-1 needle" configuration. Although not shown, hub 4 could be supplied by a manufacturer contained in a protective and sterile capsule or container where the user would peel or rip open a seal or the container itself to gain access to the sterile single dispense interface. In some instances it might be desirable to provide two or more seals for each end of the hub. The seal may allow display of information required by regulatory labeling requirements. When a needle is used to deliver the medicaments it is preferred that the hub is designed to be economical and safe for allowing the user to attach a new hub for each injection. Attachment of hub 4 to the multi-use device 10 creates a fluid connection between output needle 3 and medicaments 1 and 2.

The example in FIG. 1 uses a rotational coupling 7 to mechanically link two dose delivery assemblies 8 and 9 in such a way that rotation of single dose setter 12 allows the user to select a dose of the primary medicament 1 and automatically set a fixed or predetermined non-user settable dose of secondary medicament 2. In the embodiment illustrated, the rotational coupling 7 has been embodied as a gear train in which counter-clockwise rotation of the single dose setter causes clockwise rotation of dose dial components (not shown) within the dose delivery assemblies 8 and 9. Rotational coupling 7 may be constructed such that it moves vertically at the same rate as both of the dial components. This allows it to set and dispense both drug compounds throughout the full operational range of the device.

As well understood by those skilled in the art, it is convenient to use spindles or spindles to push on a piston or bung contained within a cartridge of medicament. As such, the dose delivery assemblies may include spindles. By varying the spindle pitches it is possible to vary the dose sizes (and dose ratio) in relation to each other. Specifically, this allows variation of the therapeutic profile to suit a specific therapy or patient requirements by providing devices with different dose ratios. The device shown in FIG. 1 could be operated as follows:

Counter-clockwise rotation of the dose setter 12 causes counter-clockwise rotation of the drive gear and clockwise rotation of both driven gears in rotational coupling 7. Clockwise rotation of both driven gears forces both dial components in dose delivery assemblies 8 and 9 to rotate in the same direction and follow a helical path out of the body of the device. This operation allows the user to set a target dose of medicament 1, but not medicament 2, which is automatically set by whatever dose is selected for medicament 1.

Initiation of the dosing phase begins with the actuation of dispense or dose button 13 by the user. This causes the dial components to rotate independently of the dose setter.

During the dosing phase, the direction of rotation of the single dose setter as well the internal components of both device mechanisms is reversed. The rotational coupling 7 moves back towards the body of the device as both dial components wind back into the mechanisms following their respective helical paths. This reversal of rotation of both mechanisms coupled with the internal overhauling of the spindles by internal drive sleeves (not shown) causes both medicaments to be dispensed in a simultaneous fashion following the fixed ratio profile defined when the user set the target dose of medicament 1.

Varying the spindle pitches of the individual device mechanisms in relation to each other may alter the relationship of the fixed ratio of medicaments. Variation of the spindle pitch changes the advance of the spindle during dispense for a given amount of rotation during setting. Differing amounts of advance between the two mechanisms has the effect of creating different dispense ratios between the mechanisms. Variation of the spindle pitches may have the effect of extending the operational window of delivery device 10 in terms of the range of fixed ratios that can be achieved. This may also assist in keeping the spindle pitch in a range that allows resetting should the device be required to be reusable. This means that multiple pen injectors each having a different therapeutic profile can be manufactured. Specifically, this allows variation of the therapeutic profile to suit a specific titration regime and ultimately individual patient requirements.

The attachment means between hub 4 and cartridge holders 5 and 6 can be any known to those skilled in the art, including threads, snap locks, snap fits, luer locks, bayonet, snap rings, keyed slots, and combinations of such connections. The connection or attachment between the hub and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary reservoir to a non-matching injection device.

The shape of the dispense device 10, including hub 4, may be generally oval and/or cylindrical or any other geometric shape suitable for hand manipulation by a user. Additionally, hub 4 could incorporate a safety shield device that would prevent accidental needle sticks and reduce the anxiety experienced by users who suffer from needle phobia. The exact design of the safety shield is not critical to Applicants' drug delivery device, however, an example design is one that is operably connected to the first and/or second reservoirs. In such a design the activation of the safety shield could unlock the drug delivery system or instigate fluid communication between the reservoirs and in some cases cause the second medicament to be dispensed prior to activating the dose button to dispense the primary medicament from the first reservoir. Another example design would physically prevent insertion of the used drug dispense interface into the patient (e.g. a single use needle-guard type arrangement).

As mentioned an example design of Applicants' drug delivery device would include cartridges to contain the medicaments. Cartridges are typically cylindrical in shape and are usually manufactured in glass, sealed at one end with a rubber bung (piston) and at the other end by a rubber septum using a metal ferrule. The dose delivery assemblies are typically powered by a manual action of the user, however, the injection mechanism may also be powered by other means such as a spring, compressed gas or electrical energy.

Figure 2:
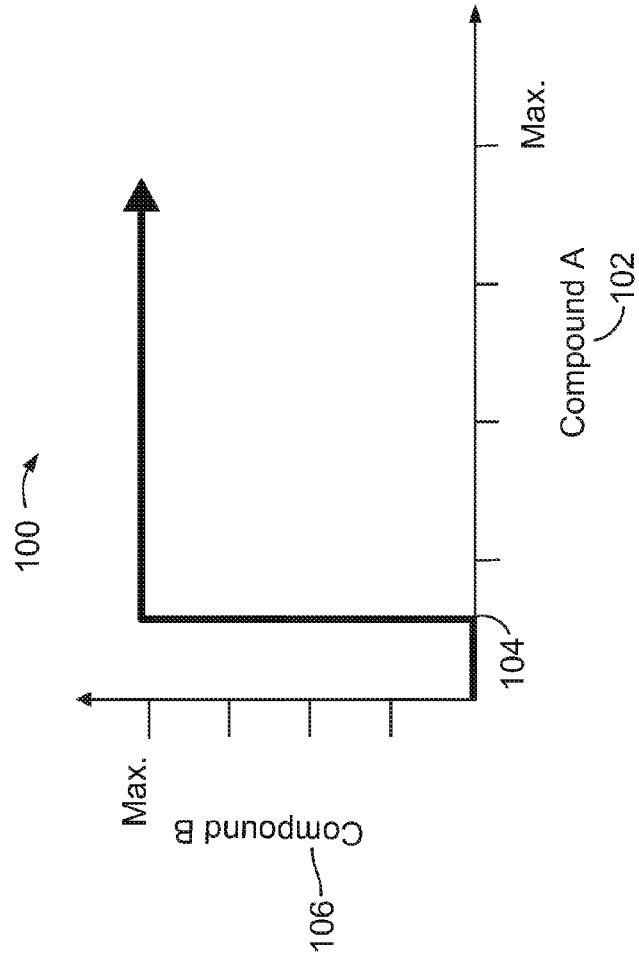
FIG. 2 illustrates an example dose profile for delivery of a first and second medicament that is achievable with a drug delivery device in accordance with an embodiment of Applicants' proposed concept.

A drug delivery device such as drug delivery device 10 may be modified so as to deliver a fixed dose of the second medicament once a minimum dose of the first medicament has been exceeded. FIG. 2 depicts an example profile 100 that follows such a therapeutic profile. As can be seen in FIG. 2, a dose of a second medicament 106 is set once a minimum dose 104 of a first medicament is set. In this example, the set dose of the second medicament 106 is fixed, and the dose of the first medicament may vary up to a maximum dose.

As mentioned above, a drug delivery device configured to deliver two medicaments may require a high dispense force to inject the two medicaments. Thus, a drug delivery device in accordance with Applicants' proposed concept may include a trigger spring to assist with the delivery of the medicament. FIG. 3 depicts an example drug delivery system 200 that includes a variable-dose spindle-type dose setting mechanism 202 connected to a fixed-dose spindle-type dose setting mechanism 204 via a mechanical coupling 206. The drug delivery system illustrated in FIG. 3 operates in a similar fashion as drug delivery system 10; however, the mechanical coupling and dose setting mechanisms are slightly altered. Further, for clarity, this Figure depicts the dose setting mechanisms and drug reservoirs without a housing around them. It should be appreciated, however, that a housing may be included to house or cover these various dose setting mechanisms and/or reservoirs. The mechanical coupling 206 includes a drive gear 208 and a driven gear 210. The drive gear 208 is capable of driving the driven gear 210. The drug delivery device 200 also includes a single dose setter 212 operably coupled to variable dose setting mechanism 202, the single dose setter having a dose button 215. The variable dose setting mechanism 202 is operably coupled to a reservoir 214 holding a first medicament 216, and the fixed dose setting mechanism 204 is operably coupled to a reservoir 218 holding a second medicament 220.

The interaction of the variable dose setting mechanism 202 and the fixed dose setting mechanism 204 via the mechanical coupling 206 causes drug delivery device 200 to set and dispense medicament according to a therapeutic profile such as profile 100 shown in FIG. 2. Further, the setting of the second medicament is automatic after a minimum dose of the first medicament is dialed. These dose setting mechanisms 202, 204 and interaction via the mechanical coupling 206 are described in greater detail below.

FIG. 4 depicts example components of the variable dose setting mechanism 202. In particular, the variable dose setting mechanism includes a dose setter 212, a dial sleeve 221, a device clutch 223, a drive sleeve 219 with drive features (e.g., engagement teeth 225), and a spindle 217. This variable dose setting mechanism 202 operates in a fashion similar to spindle-based variable dose setting mechanisms known in the art; however, this variable dose setting mechanism 202 may be attached to or engaged with the mechanical coupling 206.

FIG. 5 depicts example components of the mechanical coupling 206 of the drug delivery device 200. In particular, FIG. 5 depicts an isometric view of the mechanical coupling 206, where the drive gear 208 and driven gear 210 are coupled to one another. The drive gear 208 comprises vertical splines 222 on an inner portion 224 of the drive gear 208, and the drive gear 208 also includes clutch teeth 226. In this example, the clutch teeth 226 are located at the distal end of the drive gear 208. The variable dose setting mechanism 202 may engage with the mechanical coupling 206 via the engagement of the drive features (e.g., engagement teeth 225) on the drive sleeve 219 with the vertical splines 222 of the drive gear 208.

With reference to FIGS. 5*a-b*, rotation of the drive gear 208 may cause rotation in the opposite direction of the driven gear 210. In an example, clockwise rotation 230 of the drive gear 208 causes counter-clockwise rotation 232 of the driven gear 210. In particular, gear teeth 240 of the drive gear 208 mesh with gear teeth 242 of the driven gear 210 to facilitate the rotation. In addition, the distal portion of the drive gear 208 has clutch teeth 226 that may engage with ratchet features 234 in the body of the device 200 (see also FIG. 8). These ratchet features 234 may restrict the drive gear 208 to clockwise rotation until the secondary clutch is actuated. This restriction prevents the drive gear 208 from prematurely back winding until the initiation of the dispense process. As the drive gear 208 rotates, the clutch teeth 226 index over the ratchet teeth 234. The ratchet features 234 prevent counter-rotation of the drive gear 208 during dose setting. This may beneficially prevent premature release of the spring energy until the secondary clutch (described below) is actuated.

Figure 7:
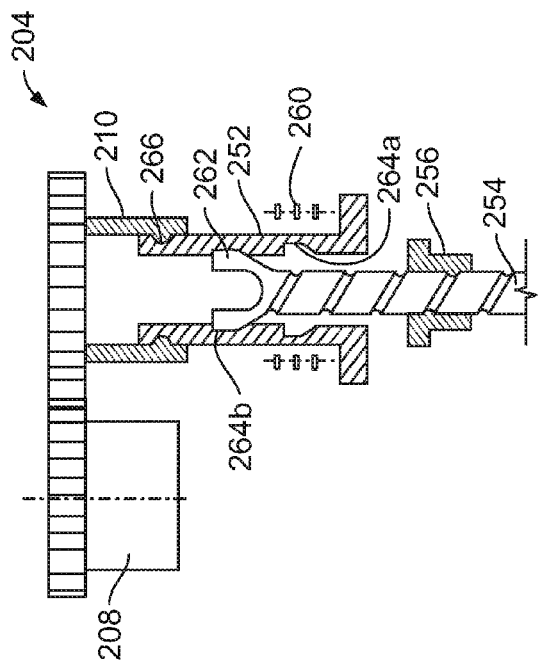
FIG. 7 is a cross-sectional view of components of the drug delivery device of FIG. 3, showing the driven gear coupled to the drive gear.
Figure 6:
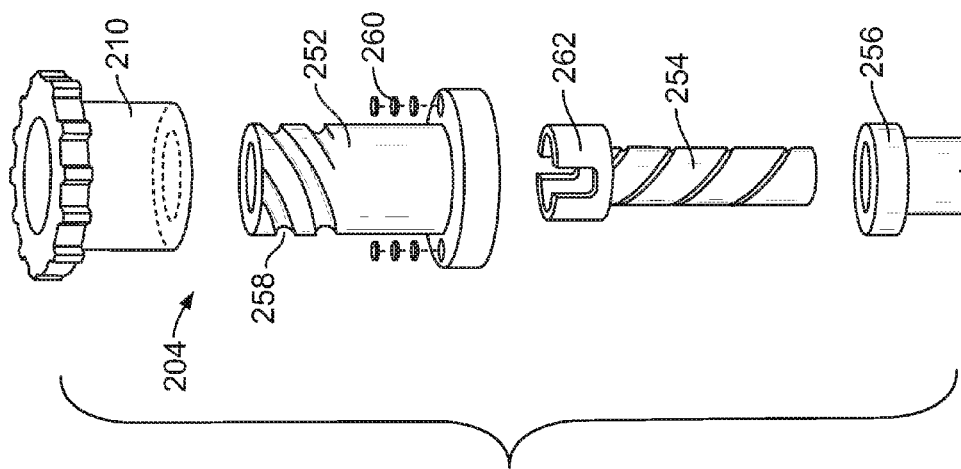
FIG. 6 is an exploded view of example components of the fixed dose setting mechanism of the drug delivery device illustrated in FIG. 3.

FIG. 6 depicts an exploded view of the fixed dose setting mechanism 204. In particular, FIG. 6 depicts the concentric arrangement of the driven gear 210, a drive collar 252, lead screw or spindle 254, and a threaded nut 256. Further, FIG. 7 depicts a cross-sectional view of the fixed dose setting mechanism 204. In this example, the driven gear 210 and the drive collar 252 are threadedly connected. In particular, threads 258 (see FIG. 6) may be connected to internal threads 266 (see FIG. 7) of the driven gear 210. Rotation of the driven gear 210 may force the drive collar 252 to lift axially as it climbs the thread (note that it may be rotationally constrained), and this action creates a force in a biasing member, or preferably as illustrated, compresses the trigger spring 260. Compression of the trigger spring thus stores mechanical energy.

The inside surface of the drive collar 252 has engagement features 264a-b (see FIG. 7) that engage flexible features 262 located at the proximal end of the spindle 254. In an example, the engagement features may be arranged as one or more helical threads. During the axial lift of the drive collar 252, the flexible features 262 are deformed by the internal engagement features of the drive collar 252 forcing it to index (i.e., the spindle 254 remains fixed axially while the drive collar 252 moves upward). The flexible features 262 and engagement features 264a-b may act like a ratchet and pawl. In other words, the flexible features flex over the immovable ratchet teeth on the inside of the drive collar. In examples where there is a helical path, the flexible features could flex and jump a thread pitch. In examples where linear features, the flexible features could jump from one pocket to the next as the drive collar climbs up the driven gear. The flexible features may be naturally 'open' and may be forced closed to move between ratchet pockets before flexing open in the next pocket. The pockets may be designed such that, when the drive collar is dispensing, the features are prevented from jumping out (i.e., a basic saw tooth profile). This 'ratcheting' mechanism formed by the engagement features 264a-b and the flexible features 262 allows a fixed dose to be metered and dispensed, but also act as the threshold at which the fixed dose is set relative to the variable dose dialed.

In the example of FIG. 7, only two sets of drive collar engagement features (i.e., 264a and 264b) are shown. However, the number of collar engagement features may vary. If a non-helical engagement feature is used, then the number of sets of collar engagement features may be one greater (i.e., N+1) than the number of fixed doses to be delivered by the fixed dose mechanism (i.e., N). By having N+1 collar engagement features, there may be a starting position to 'rest' the flexible features 262 in. In such an example, the drive collar 252 would then move back, allowing the flexible features 262 to 'snap' into the next ratchet location from which forward movement would dispense the first dose (i.e., dose 1). The next backward movement of the drive collar 252 would set and then dispense the second dose (i.e., dose 2), and so forth to the Nth dose (i.e., dose N). The provision of a start position in which the flexible arms 262 are not stressed may be beneficial as the flexible arms 262 may remain in this starting position from manufacture/assembly until first use (this could be a period of up to around 2 years or more). This resting place may minimize the risk of creep in plastic parts where the flexible features may 'take a set' in one stressed position if left there for considerable time. The resting position may also be helpful for assembly as it gives a known position into which to assembly the spindle and a datum from which to work for analysis of tolerances, etc.

Figure 8:
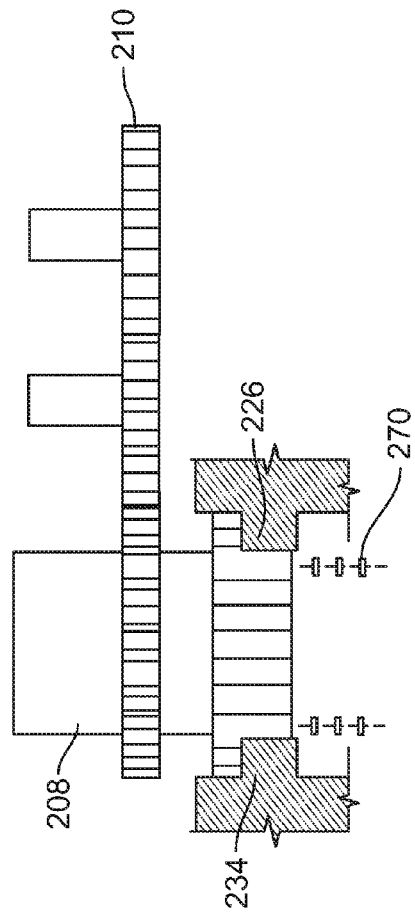
FIG. 8 is a cross-sectional view of the drive gear of FIG. 3 coupled to the driven gear of FIG. 3.

In the dispense process, the variable dose setting mechanism 202 disengages from the fixed dose setting mechanism 204. FIG. 8 depicts the arrangement of the clutch that is used to disengage the variable dose setting mechanism from the fixed dose setting mechanism. Disengagement may allow the release of the stored mechanical energy within the trigger spring 260. This release of the stored mechanical energy may assist with the dispense of the second medicament 220.

During dose setting, the clutch teeth 226 may be engaged with the ratchet features 234. However, during dispense of the first medicament 216, the drive sleeve 219 (see FIG. 4) moves downward axially. Towards the end of the dispense of the set dose of the first medicament 216, the drive sleeve 219 contacts the drive gear 208. Further axial movement of the drive sleeve 219 forces the drive gear 208 to move downwards against the action of the clutch spring 270. This action allows the clutch teeth 226 to disengage from the ratchet features 234 and thus for the drive gear 208 to disengage from the driven gear 210. This allows for the dispense of the second medicament 220 to begin, under the action of the stored energy in the fixed dose setting mechanism.

In particular, the trigger spring 260 energy pushes the drive collar 252 axially downwards. The driven gear 210 is allowed to rotate but is fixed axially and it is no longer engaged to the drive gear 208 during this action. Downward motion of the drive collar 252 may force the spindle 254 to rotate as the engagement features 264 in the drive collar 252 drive the flexible features 262 of the spindle 254. Rotation of the spindle 254 may force it to advance through the threaded nut 256 and advance the bung 274b (see FIG. 3) in the cartridge 218, thus expelling the second medicament 220. If non-helical engagement features are used instead in the drive collar, then the drive collar may advance the spindle axially and rotation of the spindle may arise from its threaded connection to the threaded nut.

An example advantage of the clutch arrangement shown in FIG. 8 is that when the user releases the dose button 215, the clutch re-engages and prevents further dispense of the second medicament. This allows the user to control the automatic injection of the second medicament. This control is possible when the second medicament is delivered on its own (i.e., sequentially after the first medicament is delivered).

The operation of the drug delivery device 200 may include the following general phases: (i) setting, (ii) initiation of dispense, (iii) dispense of the first medicament 216, and (iv) dispense of the second medicament 220. These steps or phases are described in greater detail below with reference to FIGS. 9a-c.

During dose setting, rotation of the dose setter 212 sets the variable dose of the first medicament 216 and, through the mechanical coupling 206, forces the drive collar 252 to climb the thread on the underside of the driven gear 210 and compress the trigger spring 260. At a certain amount of axial lift, the fixed dose setting mechanism 204 reaches its set point (the point at which the engagement features index over the flexible features of the spindle). At this point the drive features 225 on the drive sleeve disengage from the vertical splines 222, and this allows the variable dose setting mechanism to set larger doses of the first medicament without further rotation of the driven gear 210.

In this embodiment, it is action of setting the variable dose that sets the fixed dose. Therefore the latter is dependant upon the former. In particular, the volume of fixed dose is a function of the pitch of the 'ratchet features' 264a-b on the inside of the drive collar 252, and the drive collar 252 movement is directly dependant upon the movement of the drive gear 208 which is linked to the variable dose setting mechanism 202. Consequently, the drive collar 252 will only start to climb the driven gear 210 and consequently move the flexible features 262 from one ratchet position to the next when the variable dose is being set. Dependant upon, for example, at least (i) the size of fixed dose, (ii) mechanical advantages achievable across the gears, and (iii) threaded sections, this fixed dose could be set at a low variable set threshold. However, the fixed dose is still dependant upon at least a minimum threshold variable dose being met. Advantageously this setting threshold means that the user can take any dose of variable medicament up to the threshold without receiving the dose of fixed medicament. This could be beneficial for priming, top-up doses, etc. In some situations, this could be a therapeutic threshold below which the combination is not required. Note that in some cases, the fixed dose threshold may be the same as the smallest settable variable dose (e.g., 1 unit). In such a situation, any set dose of the variable medicament would result in a fixed dose.

The user may initiate the dispense phase by actuating the dose button 215. This allows the drive sleeve 219 to move axially back into the body of the variable dose setting mechanism and the drive features 225 to slide along the vertical splines 222 in the drive gear 208. The first medicament 216 is dispensed as the spindle 217 is overhauled by the drive sleeve 219 and forced to advance. This drives the bung 274a thus expelling the first medicament 216. The medicament 216 may be expelled through the single dispense interface 280.

The auto-assisted dispense of the second medicament may occur at various points in the dispense process. In an example, the second medicament dispense occurs after the dose of the first medicament is fully dispensed. In other examples, however, dispense of the second medicament may occur simultaneously with dispense of the first medicament. The time of dispense of the second medicament may be varied by altering when the drive gear disengages from the driven gear. Initiation of the dispense of the second medicament 220 commences when the drive features on the drive sleeve 219 force the drive gear 208 to move downwards against the clutch spring 270 (thus allowing the stored energy in the trigger spring 260 to be released) (see FIG. 9c). As mentioned above, during downward movement the clutch teeth 226 disengage from the ratchet 234 and the drive gear 208 disengages from the driven gear 210.

During dispense of the second medicament, the driven gear 210 rotates. This may cause the drive collar 252 to move downward axially (along the threads on the underside of the driven gear 210 with the assistance of the trigger spring energy). Downward motion of the drive collar 252 forces the spindle 254 to rotate as the engagement features 264 act on the flexible features of the spindle and force it around a helical path. Rotation of the spindle 254 forces the spindle 254 to advance through the threaded nut 256 and advance the bung 274b in the cartridge 218 thus expelling the medicament 220. The threaded nut 256 may be constrained from rotation and axial movement. This constraint may beneficially act to prevent the spindle from being wound out as the fixed dose is set. The medicament 220 may be expelled through the single dispense interface 280.

In an embodiment, the therapeutic profile can be further controlled by altering the design parameters of the mechanical coupling (e.g., varying the gear ratios) or varying the pitch of the fixed dose spindle. Such alterations may beneficially allow further tailoring of the therapeutic profile to meet the needs of a specific therapy or particular patient requirements.

In an example, the position of the minimum threshold point can be altered, as can the dispensed volume of the second medicament. In particular, the minimum threshold 104 at which the fixed dose setting mechanism 204 reaches its set point can be varied. For instance, the minimum threshold 104 can be varied through the variation of the mechanical properties of the mechanical coupling 206. For example, varying the relative diameters and/or the number of gear teeth 240 of the drive gear and gear teeth 242 of the driven gear will alter the point at which the set point is reached. As another example, altering the pitch of the internal threads of the driven gear will alter the point at which the set point is reached. However, it should be understood that the design should avoid the situation where the system may lock up due to the thread pitch angle creating excessive friction. In addition, the fixed dose of the second medicament can be altered by varying the spacing between the engagement features (or the thread pitch if using helical engagement features) on the drive collar. These two example design variables can be used individually or in combination to achieve the desired fixed dose set point. In combination, they may have the effect of extending the operational window of the device in terms of the range of fixed dose set points that can be achieved. Thus, multiple drug delivery devices that each have a different therapeutic profile can be manufactured. This allows variation of the therapeutic profile to suit specific titration regimes or individual patient requirements.

In an alternative embodiment, the spindle-based fixed dose setting mechanism could be replaced by a moving-rack-type mechanism. For example, with reference to FIG. 7, the spindle could be replaced by a moving rack and the threaded nut could be replaced by a non-return ratchet. This non-return ratchet would allow forward advancement of the moving rack (as it is acted upon by the drive collar through flexible features) but would not allow the moving rack to be pulled back during setting of the fixed dose (as the drive collar is pulled upwards).

In addition, although shown as a "2-to-1" needle, the injection component could be embodied as two separate needles. A separate needle would be provided for each separate medicament. In addition, the disclosed drug delivery system could be embodied in such a way as to allow for the injection of drug compounds from more than two primary packs. This would involve the addition of additional drive mechanisms and an extension of the number of dispense mechanisms operably connected to the primary dispense mechanism.

The disclosed drug delivery system may be suited towards a modular disposable or re-usable platform in terms of managing drug wastage. This is because there is a risk of one medicament being finished before the other unless there is a strict 1:1 ratio between the two medicaments. However, where each side is resettable, new primary packs can be inserted and the device can continue to be used. Possible embodiments for a modular disposable platform could, but are not limited to, involve the replacement of the entire device mechanism fitted with a new primary pack. Suitable re-engagement features may be integrated into the device platform to facilitate the alignment and fastening of the individual device mechanisms together in a robust and user friendly fashion. It is possible that such features could be arranged to define the permissible functionality of the two individual elements on their own.

A possible re-usable platform would feature spindles that could be back wound into their respective devices once they had reached the limits of travel. In addition to this functionality, the platform would feature a means of replacing both primary packs after the resetting of one or both spindles.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device to deliver two or more medicaments comprising:
   a variable dose setting mechanism, wherein the variable dose setting mechanism is operably coupled to a primary reservoir holding a first medicament;
   a fixed dose setting mechanism, wherein the fixed dose setting mechanism is operably coupled to a secondary reservoir holding a second medicament, wherein the fixed dose setting mechanism comprises a trigger biasing member;
   a single dose setter operably coupled to the variable dose setting mechanism for setting a variable dose of the first medicament;
   a mechanical coupling, wherein the mechanical coupling operably couples the variable dose setting mechanism and the fixed dose setting mechanism such that
   during dose setting, activation of the single dose setter sets a variable dose of the first medicament and thereby automatically sets a fixed dose of the second medicament, and
   wherein, during dispense, the trigger biasing member at least assists with the dispense of the fixed dose of the second medicament.

2. The drug delivery device of claim 1, wherein the trigger biasing member is a trigger spring, the mechanical coupling comprises (i) a drive gear and (ii) a driven gear, the drug delivery device further comprising:
   a drive collar that is capable of engagement with the driven gear; and
   wherein the trigger spring is operably coupled to the drive collar;
   wherein, during setting of the fixed dose, the drive gear drives the driven gear, wherein driving the driven gear causes the driven gear to lift the drive collar, and wherein lifting of the drive collar compresses the trigger spring; and
   wherein, during dispense, the drive gear and the driven gear disengage from one another, and wherein the compressed trigger spring forces the drive collar downward to at least assist with the dispense of the second medicament.

3. The drug delivery device of claim 2 wherein the drive gear comprises clutch teeth, wherein the clutch teeth are engaged with ratchet features of the drug delivery device during dose setting, and wherein the clutch teeth are disengaged from the ratchet features during dispense of the second medicament.

4. The drug delivery device of claim 3, wherein the drive gear disengages from driven gear when the clutch teeth are disengaged from the ratchet features during dispense of the second medicament.

5. The drug delivery device of claim 4, wherein the drive gear is operably coupled to a clutch spring, wherein the clutch spring ensures the clutch teeth) are engaged with the ratchet features during dose setting.

6. The drug delivery device of claim 1, wherein the fixed dose setting mechanism comprises a spindle, wherein the spindle comprises at least one flexible feature, and wherein the at least one flexible feature is coupled to the drive collar.

7. The drug delivery device of claim 6, wherein the drive collar comprises at least one engagement feature for the at least one flexible feature.

8. The drug delivery device of claim 7, wherein during lift of the drive collar, the at least one flexible feature is deformed by the at least one engagement feature forcing the spindle to index, such that the spindle remains fixed axially while the drive collar is lifted.

9. The drug delivery device of claim 7, wherein the at least one engagement feature comprises a helical engagement feature.

10. The drug delivery device of claim 7, wherein the at least one engagement feature comprises a non-helical engagement feature.

11. The drug delivery device of claim 6, further comprising a threaded nut, wherein the threaded nut is configured to engage with the spindle.

12. The drug delivery device of claim 1, wherein the variable dose setting mechanism is a rotationally driven variable dose setting mechanism, and wherein the fixed dose setting mechanism is a rotationally-driven fixed dose setting mechanism.

13. The drug delivery device of claim 1, wherein the fixed dose of the second medicament is a predefined, non-user settable dose, wherein the fixed dose of the second medicament is set at the same time as the variable dose of the first medicament.

14. The drug delivery device of claim 1, wherein the variable dose of the first medicament varies up to a maximum dose.

* * * * *